(12) United States Patent
Hartman et al.

(10) Patent No.: US 9,409,039 B2
(45) Date of Patent: Aug. 9, 2016

(54) SYSTEMS AND METHODS FOR AUTOMATIC CREATION OF DOSE PREDICTION MODELS AND THERAPY TREATMENT PLANS AS A CLOUD SERVICE

(71) Applicant: Varian Medical Systems International AG, Zug (CH)

(72) Inventors: Joona Hartman, Espoo (FI); Maria Cordero Marcos, Vantaa (FI); Esa Kuusela, Espoo (FI); Jarkko Peltola, Tuusula (FI); Janne Nord, Espoo (FI)

(73) Assignee: Varian Medical Systems International AG, Cham (CH)

( * ) Notice: Subject to any disclaimer, the term of this patent is extended or adjusted under 35 U.S.C. 154(b) by 131 days.

(21) Appl. No.: 14/040,618

(22) Filed: Sep. 27, 2013

(65) Prior Publication Data

US 2014/0350863 A1    Nov. 27, 2014

Related U.S. Application Data

(60) Provisional application No. 61/798,852, filed on May 21, 2013.

(51) Int. Cl.
*G06F 15/18* (2006.01)
*A61N 5/10* (2006.01)

(52) U.S. Cl.
CPC .............. *A61N 5/1031* (2013.01); *A61N 5/103* (2013.01); *A61N 2005/1041* (2013.01)

(58) Field of Classification Search
USPC .......................................................... 706/12
See application file for complete search history.

(56) References Cited

U.S. PATENT DOCUMENTS 7,894,574 B1 *  2/2011  Nord .................... A61N 5/1042
                                                      378/65
7,986,768 B2 *  7/2011  Nord ..................... A61N 5/103
                                                      378/65

(Continued)

FOREIGN PATENT DOCUMENTS

EP          2574374         4/2013

OTHER PUBLICATIONS

Prediction of Hemodynamic Response to Epinephrine via Model-Based System Identification Bighamian, R.; Soleymani, S.; Reisner, A.T.; Seri, I.; Jin-Oh Hahn Biomedical and Health Informatics, IEEE Journal of Year: 2016, vol. 20, Issue: 1 pp. 416-423, DOI: 10.1109/JBHI.2014.2371533 IEEE Journals & Magazines.*

(Continued)

*Primary Examiner* — Michael B Holmes

(57) ABSTRACT

The present invention proposes a method for automatically creating a dose prediction model based on existing clinical knowledge that is accumulated from multiple sources without collaborators establishing communication links between each other. According to embodiments of the claimed subject matter, clinics can collaborate in creating a dose prediction model by submitting their treatment plans into a remote computer system (such as a cloud-based system) which aggregates information from various collaborators and produces a model that captures clinical information from all submitted treatment plans. According to further embodiments, the method may contain a step where all patient data submitted by a clinic is made anonymous or the relevant parameters are extracted and condensed prior to submitting them over the communications link in order to comply with local regulations.

41 Claims, 4 Drawing Sheets

(56) References Cited

U.S. PATENT DOCUMENTS

| | | | | |
|---|---|---|---|---|
| 8,009,802 | B2* | 8/2011 | Nord | A61N 5/1031 378/65 |
| 8,121,252 | B2* | 2/2012 | Nord | A61N 5/103 378/65 |
| 8,278,633 | B2* | 10/2012 | Nord | A61N 5/1049 250/395 |
| 8,280,003 | B2* | 10/2012 | Torsti | A61N 5/1045 378/64 |
| 8,284,897 | B2* | 10/2012 | Nord | A61N 5/1037 378/65 |
| 8,295,436 | B2* | 10/2012 | Nord | A61N 5/1036 378/65 |
| 8,363,785 | B2* | 1/2013 | Nord | A61N 5/103 378/65 |
| 8,411,819 | B2* | 4/2013 | Nord | A61N 5/103 378/64 |
| 8,416,918 | B2* | 4/2013 | Nord | A61N 5/1031 378/65 |
| 8,588,369 | B2* | 11/2013 | Van Heteren | A61N 5/1031 378/208 |
| 8,693,630 | B2* | 4/2014 | Nord | A61N 5/1031 378/65 |
| 8,744,148 | B2* | 6/2014 | Nord | G06T 7/0016 382/128 |
| 8,816,307 | B2* | 8/2014 | Kuusela | H05K 999/00 250/505.1 |
| 8,835,878 | B2* | 9/2014 | Nord | A61N 5/1049 250/395 |
| 8,961,382 | B2* | 2/2015 | Nord | A61N 5/1031 600/1 |
| 9,060,698 | B2* | 6/2015 | Van Heteren | A61N 5/1031 |
| 9,138,598 | B2* | 9/2015 | Nord | |
| 2010/0233707 | A1* | 9/2010 | Buckingham | 435/6 |
| 2012/0014507 | A1 | 1/2012 | Wu et al. | |
| 2014/0270053 | A1* | 9/2014 | Larson | 378/4 |

OTHER PUBLICATIONS

Dose of dialysis predicted by continuous measurement of dialysate urea concentration Cappello, A.; Tartarini, R.; Paolini, F.; Calzavara, P Engineering in Medicine and Biology Society, 1996. Bridging Disciplines for Biomedicine. Proceedings of the 18th Annual International Conference of the IEEE Year: 1996, vol. 5 pp. 1813-1815 vol. 5.*

The Lyman and a current parallel model: are they equivalent in predicting radiation induced lung toxicity Yorke, E.; Jackson, A.; Rosenzweig, K.; Merrick, S.; Ling, C. Engineering in Medicine and Biology Society, 2000. Proceedings of the 22nd Annual International Conference of the IEEE Year: 2000, vol. 1 pp. 694-697 vol. 1.*

Machine Learning for Modeling Dose-Related Organ-at-Risk Complications after Radiation Therapy H. H. Zhang; L. Shi; R. R. Meyer; W. D. D'Souza Machine Learning and Applications, 2009. ICMLA '09. International Conference on Year: 2009 pp. 457-462, DOI: 10.1109/ICMLA.2009.55 IEEE Conference Publications.*

Experimental Characterization and Numerical Modeling of Tissue Electrical Conductivity during Pulsed Electric Fields for Irreversible Electroporation Treatment Planning R. E. Neal II; P. A. Garcia; J. L. Robertson; R. V. Davalos IEEE Transactions on Biomedical Engineering 2012, vol. 59, Issue: 4 pp. 1076-1085, DOI: 10.1109/TBME.2012.2182994.*

Computerised conformal radiation therapy—a critical process C. J. Moore Computing & Control Engineering Journal Year: 1995, vol. 6, Issue: 5 pp. 205-210, DOI: 10.1049/cce:19950501 IET Journals & Magazines.*

Predictive modeling of tumors using RP A. Kamrani; M. Azimi; E. A. Nasr Industrial Engineering and Operations Management (IEOM), 2015 International Conference on Year: 2015 pp. 1-8, DOI: 10.1109/IEOM.2015.7093789 IEEE Conference Publications.*

* cited by examiner

Exemplary Computer
System 400

SYSTEMS AND METHODS FOR AUTOMATIC CREATION OF DOSE PREDICTION MODELS AND THERAPY TREATMENT PLANS AS A CLOUD SERVICE

CLAIM OF PRIORITY

This application claims the benefit of U.S. Provisional Application No. 61/798,852, filed Mar. 13, 2013 to Hartman, et al., entitled "SYSTEMS AND METHODS FOR AUTOMATIC CREATION OF DOSE PREDICTION MODELS AND THERAPY TREATMENT PLANS AS A CLOUD SERVICE," and which is incorporated herein by reference in its entirety.

BACKGROUND OF THE INVENTION

Radiology is the branch of medical science dealing with medical imaging for the purpose of diagnosis and treatment. The practice of radiology often involves the usage of X-ray machines or other radiation devices to perform the diagnosis or administer the treatment. Other practices of radiology employ techniques that do not involve radiation, such as magnetic resonance imaging (MRI) and ultrasound. As a medical field, radiology can refer to two sub-fields, diagnostic radiology and therapeutic radiology.

Diagnostic radiology deals with the use of various imaging modalities to aid in the diagnosis of a disease or condition in a subject. Typically, a wide beam of X-rays at a relatively low dosage is generated from a radiation source and directed towards an imaging target. An imager positioned on the opposite side of the source with respect to the imaging target receives the incident radiation and an image is generated based on the received radiation. Newer technology and advanced techniques allow for improved image collection with the application of computerized tomography (CT) to medical imaging techniques. Conventional medical imaging processes involving CT scans typically produce a series of 2-dimensional images of a target area which can be subsequently combined using computerized algorithms to generate a 3-dimensional image or model of the target area.

Therapeutic radiology or radiation oncology involves the use of radiation to treat diseases such as cancer through the directed application of radiation to targeted areas. In radiation therapy, radiation is applied (typically as a beam) to one or more regions of the targeted area at pre-specified dosages. Since the radiation can be potentially harmful, extensive treatment planning may be conducted, sometimes far in advance of the actual treatment sessions, to pinpoint the exact location(s) to apply the beam, and to limit unnecessary exposure to the radiation to other areas in the subject. The treatment planning phase may include the performance of CT scanning or other medical imaging techniques to acquire image data that can be subsequently used to precisely calculate the proper position and orientation of the subject, location of one or more target areas within the subject, and to predict the dosage(s) of the radiation to be applied during therapy.

Traditionally, radiotherapy treatment plans are created by a human operator by manually defining optimization objectives to achieve a clinically acceptable plan. Recently, human operators can produce treatment plans automatically by utilizing existing clinical knowledge that is captured by an algorithm by using a training phase that requires the human operator to select examples for the algorithm.

Automatic planning by existing systems relies on the human operator to train the algorithm, which requires that the human operator has access to existing radiotherapy treatment plans. However, this may be prohibitive for clinics that are only starting to establish radiotherapy treatment. The problem is exacerbated since all of the data used to train an algorithm has to be accessible by the human operator responsible for training the algorithm and requires establishing communication links between all participants and knowledge bases. For beginning clinics and practices where such information is not available, automatic planning may not be an option at all.

Furthermore, once created, a treatment plan is often further optimized based on a variety of factors, such as the treatment condition, the patient, and available resources. However, optimizing a treatment plan manually is time consuming as the optimization objectives are iteratively changed and the resulting dose distribution may be repeatedly re-evaluated until an optimal plan is achieved.

A critical component of treatment planning is predicting the dosage and dose distribution of the radiation to be applied to the patient. In knowledge based dose prediction, information from previously planned radiation treatments are used to gain knowledge of what is an achievable dose distribution in a new case without performing the actual planning. One approach to knowledge based dose prediction is to use a set of the previously planned cases to create a prediction model that could then be used (without needing to store all information related to this training set) to predict the dose for a new case.

Typically, a prediction model contains information that is necessary to predict the dose distribution achieved for a given patient geometry if planning is performed according to techniques, objectives and trade-offs described by the model. These predictions can be transformed into optimization objectives that when used in combination with an optimization algorithm, produce a complete radiotherapy treatment plan. However, accumulating a library of treatment plans that covers a representative portion of patient variety in a single clinic may be difficult or impossible for certain treatment techniques due to their rarity. Transmitting patient sensitive data between multiple participants may be difficult due to local regulations.

Each model typically has certain regions where the model's predictions are valid; however, if geometric parameters of the new case differ too much from the geometric parameters planned by the training set, the dose predictions may no longer be reliable. In some instances, a clinic may have several models to cover a large variety of different regions. Sample treatment plans and models may also be shared between clinics, thereby increasing the number of available models even more. However, sharing individual models between multiple clinics results in clinics having possibly tens or hundreds of different, but possibly overlapping models. This may make clinical use of shared models tedious and inefficient.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

What is proposed is a method for automatically creating a dose prediction model based on existing clinical knowledge that is accumulated from multiple sources without collaborators establishing communication links between each other. According to embodiments of the claimed subject matter, clinics can collaborate in creating a dose prediction model by submitting their treatment plans into a remote computer system (such as a cloud-based system) which aggregates information from various collaborators and produces a model that captures clinical information from all submitted treatment plans. According to further embodiments, the method may contain a step where all patient data submitted by a clinic is made anonymous or the relevant parameters are extracted and condensed prior to submitting them over the communications link in order to comply with local regulations.

According to another aspect of the present invention, a method is proposed wherein a user can submit a patient geometry description into a software program residing on a remote computer system (later referred to as cloud service), which automatically generates and returns a radiotherapy treatment plan to the user based on a prediction model. According to such embodiments, a prediction model from a stored bank of prediction models is selected, based on geometrical characteristics of the patient case for example. A dose distribution is predicted based on the selected prediction model. Optimization objectives are then determined based on the predicted dose distribution and a treatment plan is generated based on the determined optimization objectives.

In further embodiments, the method may also contain steps where dose prediction models are created by clinics and made available as a cloud service for other clinics, without the need for sharing confidential patient information. According to these embodiments, a treatment plan may be automatically created on a remote computer system that requires no configuration or manual training of the dose prediction models by the end-user, thereby reducing potential delays and inefficiencies resulting from unavailable treatment planners.

BRIEF DESCRIPTION OF THE DRAWINGS

The accompanying drawings are incorporated in and form a part of this specification. The drawings illustrate embodiments. Together with the description, the drawings serve to explain the principles of the embodiments.

DETAILED DESCRIPTION

Figure 1:
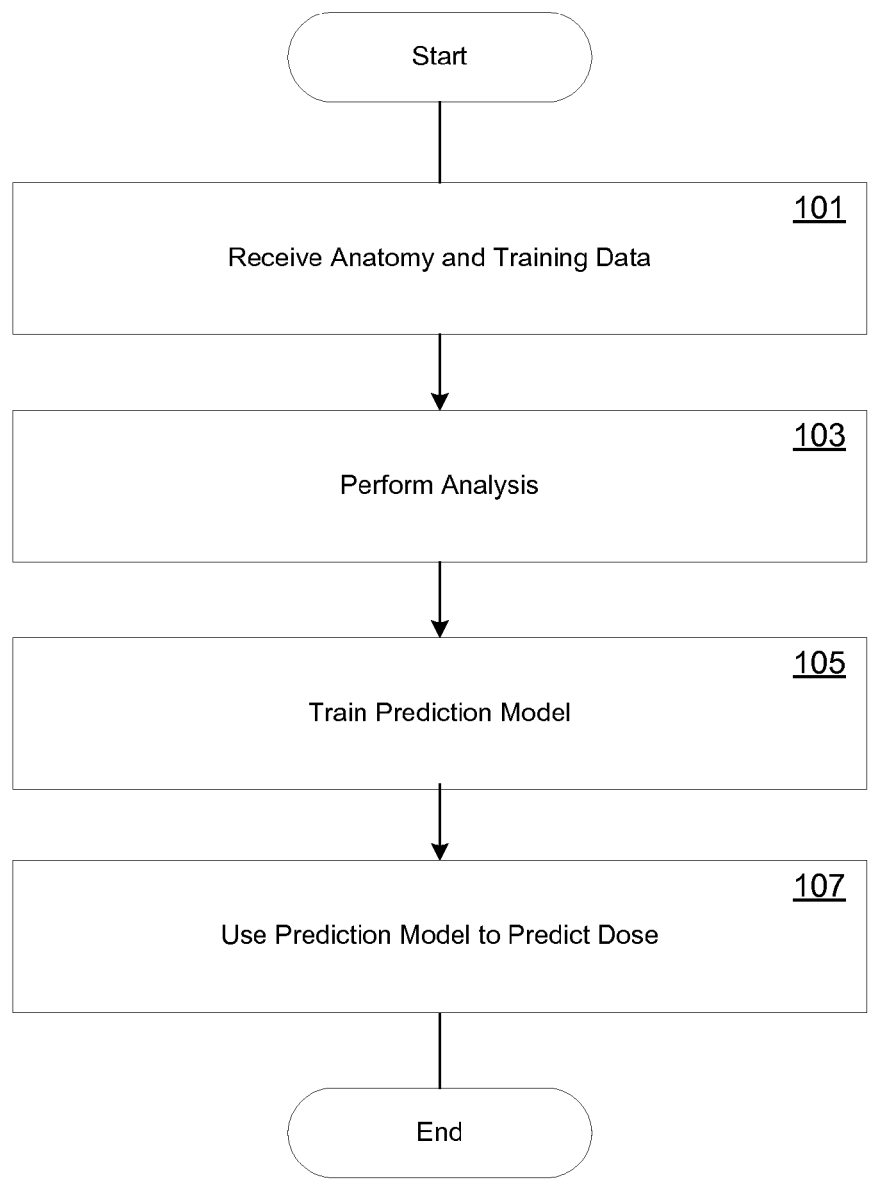
FIG. 1 depicts a flowchart of an exemplary process for selecting a training set of data for a dose prediction model, in accordance with various embodiments of the present invention.

Reference will now be made in detail to the preferred embodiments of the claimed subject matter, a method and system for the use of a radiographic system, examples of which are illustrated in the accompanying drawings. While the claimed subject matter will be described in conjunction with the preferred embodiments, it will be understood that they are not intended to limit these embodiments. On the contrary, the claimed subject matter is intended to cover alternatives, modifications and equivalents, which may be included within the spirit and scope as defined by the appended claims.

Furthermore, in the following detailed descriptions of embodiments of the claimed subject matter, numerous specific details are set forth in order to provide a thorough understanding of the claimed subject matter. However, it will be recognized by one of ordinary skill in the art that the claimed subject matter may be practiced without these specific details. In other instances, well known methods, procedures, components, and circuits have not been described in detail as not to obscure unnecessarily aspects of the claimed subject matter.

Some portions of the detailed descriptions which follow are presented in terms of procedures, steps, logic blocks, processing, and other symbolic representations of operations on data bits that can be performed on computer memory. These descriptions and representations are the means used by those skilled in the data processing arts to most effectively convey the substance of their work to others skilled in the art. A procedure, computer generated step, logic block, process, etc., is here, and generally, conceived to be a self-consistent sequence of steps or instructions leading to a desired result. The steps are those requiring physical manipulations of physical quantities. Usually, though not necessarily, these quantities take the form of electrical or magnetic signals capable of being stored, transferred, combined, compared, and otherwise manipulated in a computer system. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the following discussions, it is appreciated that throughout the present claimed subject matter, discussions utilizing terms such as "storing," "creating," "protecting," "receiving," "encrypting," "decrypting," "destroying," or the like, refer to the action and processes of a computer system or integrated circuit, or similar electronic computing device, including an embedded system, that manipulates and transforms data represented as physical (electronic) quantities within the computer system's registers and memories into other data similarly represented as physical quantities within the computer system memories or registers or other such information storage, transmission or display devices.

Accordingly, embodiments of the claimed subject matter provide a method and system for automatic generation of treatment plans and dose prediction models on remote cloud computing components.

Configuring a DVH Estimation Model

FIG. 1 depicts a flowchart of a process 100 for configuring a dose prediction model. Steps 101 to 107 describe exemplary steps comprising the process 100 depicted in FIG. 1 in accordance with the various embodiments herein described. In one embodiment, the process 100 may be implemented in whole or in part as computer-executable instructions stored in a computer-readable medium and executed by a processor in a computing device.

According to one aspect, the dose prediction model may be used to predict dose parameters for a treatment plan corresponding to a radiation therapy patient. In one or more embodiments, the dose prediction model may be implemented as a dose-volume histogram (DVH) estimation model, where the predicted quantity is a dose volume histogram. In further embodiments, the prediction model may also generate a prediction based on a distance to target (DTH) histogram, which expresses the distance from a region or structure (such as an organ-at-risk) to a radiation target. In still further embodiments, the dose prediction model may be implemented as any other model suitable for predicting dosage (as a dose histogram, or spatial three dimensional dose distribution) for a radiotherapy treatment plan.

In one or more embodiments, a DVH estimation model can be configured by selecting a group of appropriate treatment plans from a treatment plan database (step 101). Ideally, the plans should be of high-quality, and sufficiently similar to a treatment being planned for a radiation target/patient, for example, in regard to the treatment area, field geometry, and fractionation. The system analyzes the patient anatomy (including, in some instances, anatomical information for each organ-at-risk (OAR)) and DVH values selected from this training set of plans (step 103), and trains a mathematical DVH estimation model (step 105) based on the patient anatomy and dose volume histogram values. Once trained, the prediction model may be used to predict (step 109) the dose parameters for the treatment plan of the radiation therapy patient. According to one or more embodiments, the process performs uniformity checks to the plans in a training set, and reports any significant deviations. When applying the model to a plan, the algorithm also checks whether the patient anatomy in the plan matches the training set.

DVH Estimation Model Training

Figure 2:
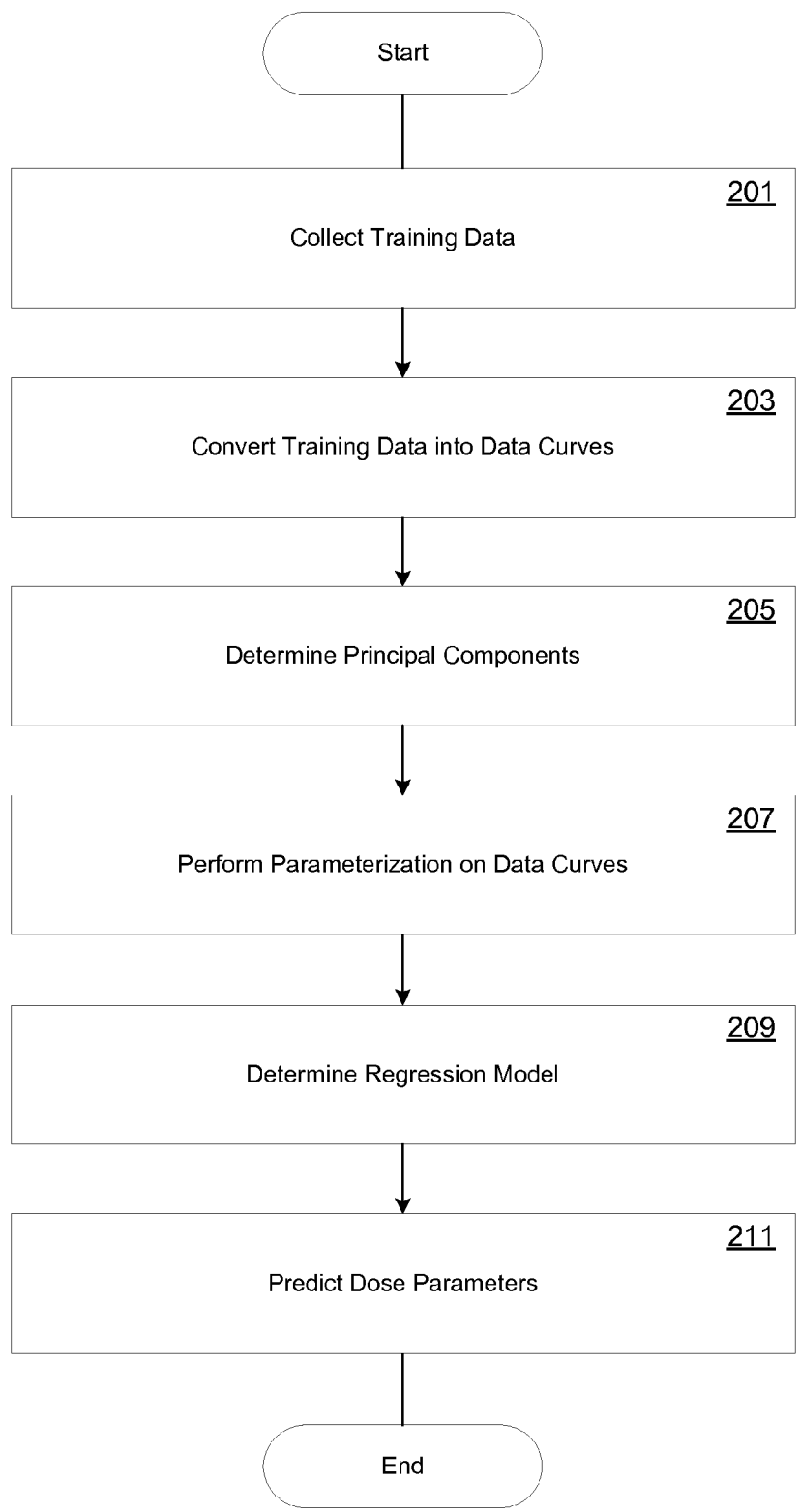
FIG. 2 depicts a flowchart of an exemplary process for training a dose prediction model, in accordance with various embodiments of the present invention.

Once the set of training data is selected, a prediction model may be trained (i.e., refined) to generate more precise dose estimations for the radiation therapy treatment being planned. FIG. 2 depicts the process 200 for training a prediction model. Steps 201 to 211 describe exemplary steps comprising the process 200 depicted in FIG. 2 in accordance with the various embodiments herein described. In one embodiment, the process 200 may be implemented in whole or in part as computer-executable instructions stored in a computer-readable medium and executed by a processor in a computing device.

In one or more embodiments, an implementation of a DVH estimation begins by analyzing the training set of data (selected at step 101) and parsing the data to collect structure sets (containing spatial information of various organs and the target), previously optimized treatment plans, and corresponding 3D dose distributions from multiple patients from the training set of data (step 201). In further embodiments, the estimation model may be used to convert (step 203) the structure sets into one or more data curves. For example, geometric information in a structure set can be converted into organ specific DTH curves. Likewise, a dose matrix may be converted into organ-specific DVH curves. These curves can be further parameterized (step 205) by first determining the principal components of the curves (e.g., structures) and the parameterization of the curves based on the determined principal components (step 207). Once parameterization is performed, a regression model can be determined (209) and used to identify how DVH parameters can be predicted based on DTH parameters (211). In one or more embodiments, a trained DVH model may include: 1) a list of treatment plans included in the model training set; 2) an identified plurality of principal components for a DVH and DTH for all organ at risk (OAR) structures in the model; 3) coefficients for a regression model; and 4) the mean and standard deviation for each anatomical feature in the training set.

According to various embodiments, parameterization of structures in a treatment plan may include generating a distance to target histogram (DTH). The parameter set related to each structure may include the principal components of a DTH; anatomical features, such as relative overlap volume, relative out-of-field volume, absolute OAR volume, and absolute target volume. According to further embodiments, a regression model may be generated as the relation between structure parameters and dose parameters in a training set. In still further embodiments, a separate regression model for each DVH principal component (e.g., each structure and dose) and for each OAR structure.

In one or more embodiments, in addition to creating DVH models, pre-constructed models within the system can be referenced for use in planning, validation, and optimization. In an embodiment, the models can be stored and shared within a clinic, or with other clinics. Sharing may be performed by hosting the stored data sets and/or constructed models in a network, such as a cloud infrastructure, accessible to remote users/clinics. By storing the data in cloud service infrastructures, data may be shared among a larger number of treatment planners and providers, without the need for each treatment center to acquire and maintain costly equipment. Moreover, each treatment center may control the amount and nature of the data shared, to preserve anonymity and confidentiality for their patients, for example.

Knowledge-Based Planning

Once constructed, a DVH Estimation model can be used as an aid in knowledge-based treatment planning. Knowledge-based treatment planning allows the application of knowledge derived from existing clinical patient cases to the treatment of new patients. The knowledge can be in the form of clinical protocols, templates, and model libraries (for contours and treatment plans). In particular DVH estimation models may be especially helpful by when creating new treatment plans and/or evaluating treatment plans.

In an embodiment, a treatment planning system includes a DVH Estimation tool, which uses the dose and patient anatomy information from existing plans to estimate the dose distribution in new plans. By using this tool, a user is able to generate optimization objectives and estimated DVH ranges for the structures (e.g., organs) in a treatment plan. The estimated DVH values may also be used as a starting point for treatment planners and provide assurances that a treatment plan is consistent with past experience. By applying the DVH Estimation solutions provided herein, a consistent level of quality can be maintained among treatment plans simply and effectively. The tool also reduces the number of optimization and evaluation iterations typically required during the generation of a treatment plan.

Figure 3:
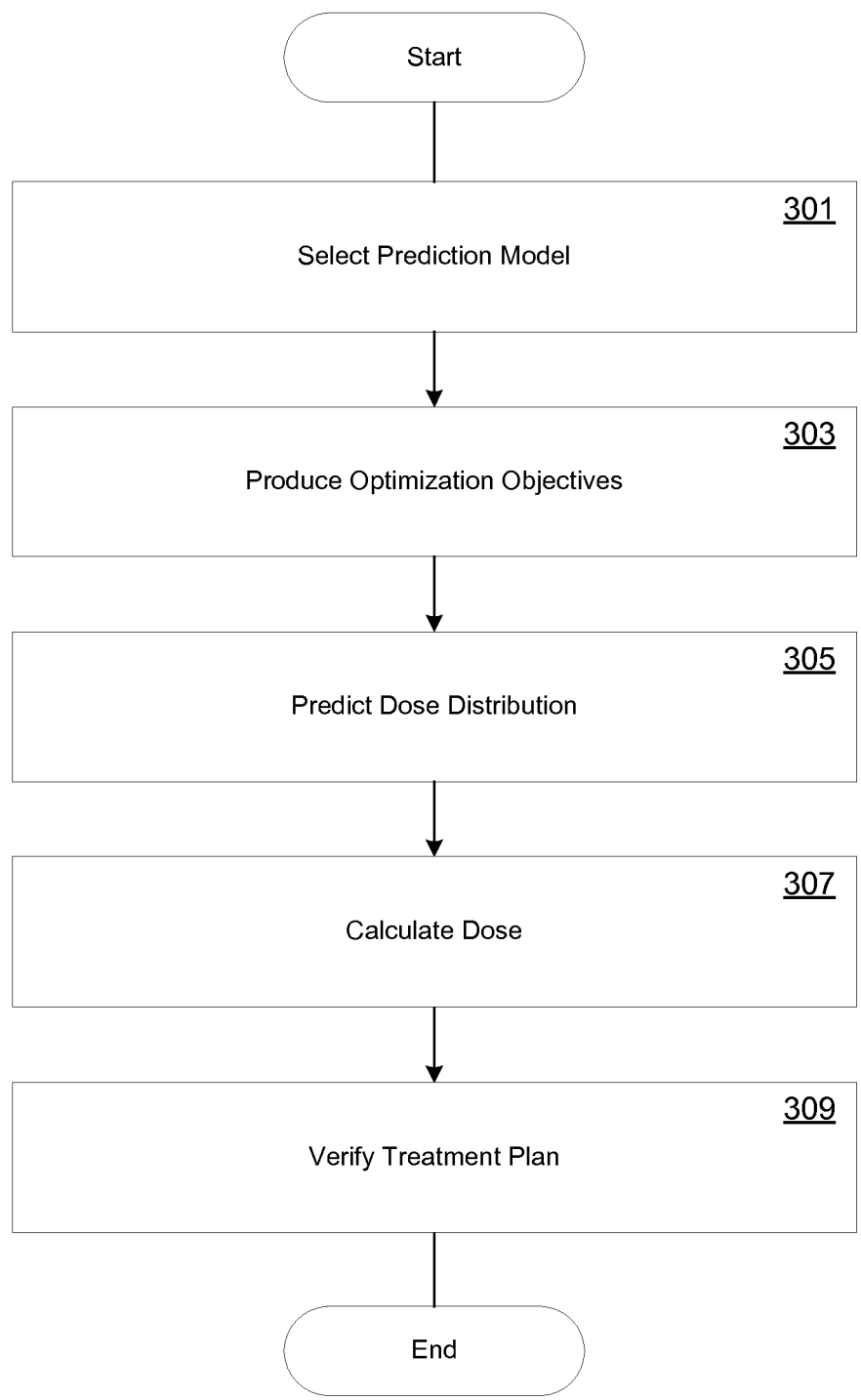
FIG. 3 depicts a flowchart of an exemplary process for automatically generating a treatment plan based on a dose prediction model.

FIG. 3 depicts a flowchart of a process 300 for automatically generating a treatment plan based on a prediction model. Steps 301 to 309 describe exemplary steps comprising the process 300 depicted in FIG. 3 in accordance with the various embodiments herein described. In one embodiment, the process 300 may be implemented in whole or in part as computer-executable instructions stored in a computer-readable medium and executed by a processor in a computing device.

In an embodiment, a prediction model is selected (step 301) from a library or storage base of pre-generated prediction models. The prediction model may, for example, comprise a DVH estimation model. Selection of the prediction model may be performed automatically, based on shared characteristics between the target of the treatment plan being generated and the treatment targets of treatment plans used to generate the selected prediction models. These characteristics may include, for example, a shared treatment type, target structure or regions, and set of organs-at-risk, etc. According to alternate embodiments, the user may also manually select the appropriate model for the planned treatment.

Once selected, the model(s) may be used to automatically create optimization objectives for a dose distribution (step 303), and automatically predict a dose distribution (step 305) for a treatment plan. In one embodiment, the dose distribution may be predicted as one or more estimated DVH ranges for the relevant anatomical structures involved in the treatment based on the predicted dose distribution. In one or more embodiments, the estimated DVHs are available for both the treatment plan (radiation) target, as well as the organs at risk (OAR). Calculation of the dose parameters may be subsequently refined in the current treatment plan in order to achieve the optimization objectives. Once the optimization is complete, a predicted dose can be calculated (step 307), after which the shapes and doses of the treatment plan may be compared (step 309) with the estimated DVH ranges for additional verification.

Automated Cloud Based Services

According to various embodiments, the processes of automatic creation of dose prediction models and automatic treatment planning may each (or both) be performed by a user remotely from the memory and processing centers (e.g., servers) performing the computations. In such embodiments, an authorized user of a computing device may access and manipulate the DVH modeling and stored treatment plan data via a network connection, e.g., the Internet. In further embodiments, the computing systems in which the data is processed and/or information (pre-constructed models, training set data, therapy plans) is stored may be implemented as cloud computing components. According to these embodiments, the computational resources required to host, maintain, and service the data and applications may be dynamically provisioned, and similarly reduced, as need and resource demands fluctuation with use.

According to an embodiment, a dose prediction model may be generated (as described above) by submitting treatment plans into a remote computer system, such as a server or virtual server of a cloud computing service. Once the data from various collaborators has been collected, the data is mined, and organized (according to various properties pertaining to patient condition, geometries, etc.). A model is then generated that captures the clinical information from all or a portion of the submitted treatment plans. According to further embodiments, patient confidentiality and anonymity may be preserved by extracting or condensing certain parameters, either prior to submission of the treatment plans, or via an automated data filtering process.

Once a dose prediction model is generated, the model may be used during an automatic treatment planning process. According to an embodiment, a treatment plan may be automatically generated with data hosted and/or processing performed on a remote computing device (such as a cloud server) by establishing a connection between the user and the cloud service provider. The user (if authorized) may then be prompted to select a prediction model from a composite storage base of pre-constructed prediction models. Selection may be based, at least partially, on characteristic similarities between the patient case and the prediction model, such as geometries, condition, etc.

Once the prediction model is selected, the dose distribution may be predicted, based on the selected model. Subsequently, optimization objectives based on the dose prediction may be produced, and a treatment plan based on the optimization objectives is then created.

Exemplary Computing System

Figure 4:
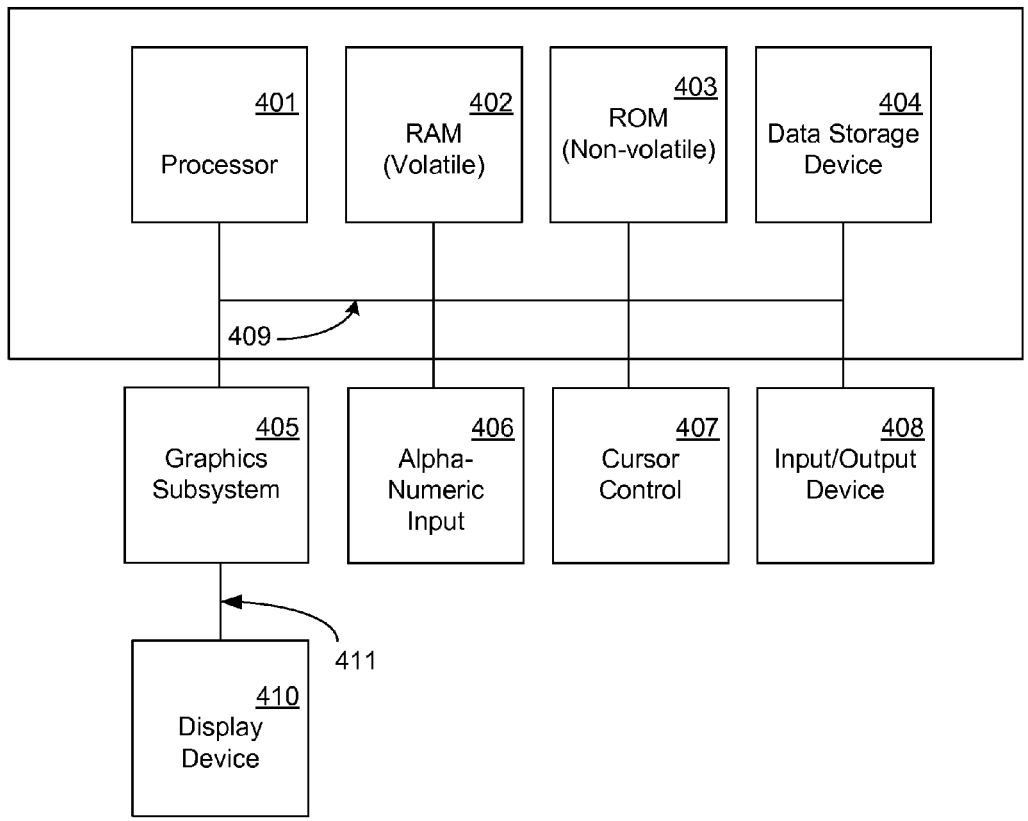
FIG. 4 depicts an exemplary computing environment, in accordance with embodiments of the present invention.

As presented in FIG. 4, an exemplary system 400 upon which embodiments of the present invention may be implemented includes a general purpose computing system environment, such as a computer operated by a remote user, or a server or virtual server of a cloud computing infrastructure. Imaging device 409, depicted in FIG. 4 and described above may, for example, be implemented as a computing system. In its most basic configuration, computing system 400 typically includes at least one processing unit 401 and memory, and an address/data bus 409 (or other interface) for communicating information. Depending on the exact configuration and type of computing system environment, memory may be volatile (such as RAM 402), non-volatile (such as ROM 403, flash memory, etc.) or some combination of the two.

Computer system 400 may also comprise an optional graphics subsystem 405 for presenting information to the computer user, e.g., by displaying information on an attached display device 410, connected by a video cable 411. According to embodiments of the present claimed invention, the graphics subsystem 405 may be coupled directly to the display device 410 through the video cable 411. A graphical user interface of an application for displaying images generated by a medical imaging device described above with respect to FIG. 1, and executing in the computer system 400 may be generated in the graphics subsystem 405, for example, and displayed to the user in the display device 410. In alternate embodiments, display device 410 may be integrated into the computing system (e.g., a laptop or netbook display panel) and will not require a video cable 411.

Additionally, computing system 400 may also have additional features/functionality. For example, computing system 400 may also include additional storage (removable and/or non-removable) including, but not limited to, magnetic or optical disks or tape. Such additional storage is illustrated in FIG. 4 by data storage device 407. Computer storage media includes volatile and nonvolatile, removable and non-removable media implemented in any method or technology for storage of information such as computer readable instructions, data structures, program modules or other data. RAM 402, ROM 403, and data storage device 407 are all examples of computer storage media.

Computer system 400 also comprises an optional alphanumeric input device 406, an optional cursor control or directing device 407, and one or more signal communication interfaces (input/output devices, e.g., a network interface card) 409. Optional alphanumeric input device 406 can communicate information and command selections to central processor 401. Optional cursor control or directing device 407 is coupled to bus 409 for communicating user input information and command selections to central processor 401. Signal communication interface (input/output device) 409, also coupled to bus 409, can be a serial port. Communication interface 409 may also include wireless communication mechanisms. Using communication interface 409, computer system 400 can be communicatively coupled to other computer systems over a communication network such as the Internet or an intranet (e.g., a local area network), or can receive data (e.g., a digital television signal).

In the foregoing specification, embodiments have been described with reference to numerous specific details that may vary from implementation to implementation. Thus, the sole and exclusive indicator of what is the invention, and is intended by the applicant to be the invention, is the set of claims that issue from this application, in the specific form in which such claims issue, including any subsequent correction. Hence, no limitation, element, property, feature, advantage, or attribute that is not expressly recited in a claim should limit the scope of such claim in any way. Accordingly, the specification and drawings are to be regarded in an illustrative rather than a restrictive sense.

What is claimed is:

1. A method for selecting a set of data for a dose prediction model, the method comprising:
   receiving a set of patient anatomy data and a set of training data, the training data comprising a plurality of treatment plans selected from a treatment plan database based on a similarity of the plurality of treatment plans with the set of patient anatomy data;

performing an analysis on the set of patient anatomy data and the set of training data;

training a dose prediction model based on the analysis; and predicting a plurality of dose parameters for a radiation therapy treatment plan by applying the dose prediction model to the set of patient anatomy data;

wherein the receiving, the performing, the training, and the predicting are performed in an application executed by a processor of a computing device.

2. The method according to claim 1, wherein the plurality of treatment plans comprises a radiation treatment plan.

3. The method according to claim 1, wherein training the dose prediction model comprises performing a DVH estimation with a DVH estimation model comprising a plurality of DVH values.

4. The method according to claim 3, wherein performing the analysis comprises:

identifying a plurality of organs at risk (OAR) comprised in the plurality of treatment plans;

analyzing anatomical information for the plurality of OAR; and modeling an effect on an OAR based on the plurality of DVH values.

5. The method according to claim 1, further comprising performing a plurality of uniformity checks on the set of training data.

6. The method according to claim 1, wherein the set of training data comprises a structure set and an absolute dose data.

7. The method according to claim 1, further comprising storing the dose in a knowledge base comprising a plurality of pre-generated dose prediction models.

8. The method according to claim 7, wherein the plurality of pre-dose prediction models comprises a plurality of DVH estimation models generated at a plurality of remote sites.

9. The method according to claim 7, wherein the knowledge base comprises a central storage device, the central storage device being accessible to a plurality of computing devices at the plurality of remote sites.

10. The method according to claim 9, wherein the central device comprises a cloud infrastructure component.

11. The method according to claim 1, wherein training the dose prediction model comprises:

analyzing the set of training data;

converting the set of training data into a plurality of data curves;

determining a plurality of principal components based on the plurality of data curves;

performing a parameterization on the plurality of data curves; and determining a regression model for the plurality of data curves.

12. The method according to claim 11, wherein predicting the plurality of dose parameters for a radiation therapy treatment plan comprises predicting the plurality of dose parameters based on the regression model.

13. The method according to claim 11, wherein the set of training data comprises at least one of the group consisting of:

a plurality of structure sets comprising spatial information of a plurality of organs and a target of the treatment plan;

a plurality of pre-optimized treatment plans; and a corresponding 3D dose distribution from a plurality of patients of the plurality of previously-optimized treatment plans.

14. The method according to claim 13, wherein converting the set of training data into a plurality of data curves comprises converting geometric information in the plurality of structure sets into a plurality of organ-specific distance-to-target histogram curves.

15. The method according to claim 13, wherein converting the set of training data into a plurality of data curves comprises converting a plurality of dose matrices comprised in the plurality of structure sets into a plurality of organ-specific dose-volume histogram curves.

16. The method according to claim 12, wherein performing the parameterization on the plurality of data curves comprises:

determining a plurality of structures from the plurality of structure sets; and determining a plurality of dose parameters from a plurality of dose matrices.

17. The method according to claim 11, wherein performing the parameterization on the plurality of data curves comprises generating a parameter set corresponding to a structure of the plurality of structure sets, a parameter set being comprised from at least one from the group consisting of:

a plurality of principal components of the DTH;

a relative overlap volume;

a relative out-of-field volume;

an absolute organ at risk volume; and an absolute target volume.

18. The method according to claim 11, wherein training the dose prediction model comprises generating a trained dose prediction model from the dose prediction model, the trained dose prediction model comprising at least one of the following;

a list of treatment plans comprised in the set of training of data;

an identified plurality of principal components for a DVH and a DTH for a plurality of OAR structures comprised in the dose prediction model;

a plurality of coefficients for a regression model based on the trained dose prediction model; and a mean and standard deviation for a plurality of anatomical features comprised in the training set of data.

19. A method for automatically predicting a dose distribution in a radiotherapy treatment plan, the method comprising:

selecting a dose prediction model from a plurality of dose prediction models based on a plurality of characteristics;

predicting a dose distribution based on the dose prediction model;

producing a plurality of optimization objectives based on the dose distribution;

creating a patient treatment plan based on the optimization objectives, and verifying the patient treatment plan with the dose prediction model, wherein the predicting, the producing, and the creating is performed in a first computing system, further wherein the selecting is performed by a user through a user interface executing on a second computing system remote from the first computing system.

20. A system for storing a plurality of dose prediction models, the system comprising:

a shared library of treatment data, the library of treatment data comprising a plurality of pre-generated treatment plans;

a plurality of computing devices, a first computing device of the plurality of computing devices comprising:

a memory configured to store a patient anatomical data;

a processor configured to execute an application, the application being configured to apply a dose prediction model to the patient anatomical data and to predict a dose distribution to a patient corresponding to the patient anatomical data, wherein the dose prediction model is trained by analyzing a selection of treatment plans from the plurality of pre-generated treatment plans, further wherein the shared library of treatment data comprises a cloud storage component communicatively coupled to the plurality of computing devices.

21. The method according to claim 19, wherein the dose prediction model comprises a DVH estimation model comprising a plurality of DVH values.

22. The method according to claim 21, wherein the dose prediction model comprises:
   an identification of a plurality of organs at risk (OAR) comprised in the treatment plan;
   an analysis of anatomical information for the plurality of OAR; and
   a model of an effect on an OAR based on the plurality of DVH values.

23. The method according to claim 21, wherein the plurality of dose prediction models comprises a plurality of DVH estimation models generated at a plurality of remote sites.

24. The method according to claim 23, wherein the plurality of does predictions models are stored in a knowledge base comprising a central storage device, the central storage device being accessible to a plurality of computing devices at the plurality of remote sites.

25. The method according to claim 24, wherein the central device comprises a cloud infrastructure component.

26. The method according to claim 22, wherein the dose prediction model is trained from a set of training data by analyzing the set of training data, converting the set of training data into a plurality of data curves, determining a plurality of principal components based on the plurality of data curves, performing a parameterization on the plurality of data curves, and determining a regression model for the plurality of data curves.

27. The method according to claim 26, wherein the set of training data comprises at least one of the group consisting of:
   a plurality of structure sets comprising spatial information of a plurality of organs and a target of the treatment plan;
   a plurality of pre-optimized treatment plans; and
   a corresponding 3D dose distribution from a plurality of patients of the plurality of previously-optimized treatment plans.

28. The method according to claim 26, wherein converting the set of training data into a plurality of data curves comprises converting geometric information in the plurality of structure sets into a plurality of organ-specific distance-to-target histogram curves.

29. The method according to claim 26, wherein converting the set of training data into a plurality of data curves comprises converting a plurality of dose matrices comprised in the plurality of structure sets into a plurality of organ-specific dose-volume histogram curves.

30. The method according to claim 26, wherein performing the parameterization on the plurality of data curves comprises:
   determining a plurality of structures from the plurality of structure sets; and
   determining a plurality of dose parameters from a plurality of dose matrices.

31. The method according to claim 30, wherein performing the parameterization on the plurality of on the plurality of data curves comprises generating a parameter set corresponding to a structure of the plurality of structure sets, a parameter set being comprised from at least one from the group consisting of:
   a plurality of principal components of the DTH;
   a relative overlap volume;
   a relative out-of-field volume;
   an absolute organ at risk volume; and
   an absolute target volume.

32. The method according to claim 26, wherein the dose prediction model comprises at least one of the following;
   a list of treatment plans comprised in the set of training of data;
   an identified plurality of principal components for a DVH and a DTH for a plurality of OAR structures comprised in the dose prediction model;
   a plurality of coefficients for a regression model based on the dose prediction model; and
   a mean and standard deviation for a plurality of anatomical features comprised in the training set of data.

33. The system according to claim 20, wherein the application is further configured to select a treatment plan from the plurality of pre-generated treatment plans based on the predicted dose distribution for the patient.

34. The system according to claim 20, wherein the dose prediction model comprises a DVH estimation model comprising a plurality of DVH values.

35. The system according to claim 34, wherein the dose prediction model comprises:
   an identification of a plurality of organs at risk (OAR) in the patient anatomical data based on at least one treatment plan of the plurality of treatment plans;
   an analysis of anatomical information for the plurality of OAR; and
   a model of an effect of an OAR on the plurality of DVH values.

36. The system according to claim 34, wherein the first computing device is remote from other computing devices of the plurality of computing devices.

37. The system according to claim 36, wherein the DVH estimation model is one of a plurality of DVH estimation models.

38. The system according to claim 37, wherein the plurality of DVH estimation models are generated by the other computing devices of the plurality of computing devices, and stored in the shared library of treatment data.

39. The system according to claim 32, wherein the dose prediction model is further trained by converting the selection of treatment plans into a plurality of data curves, determining a plurality of principal components based on the plurality of data curves, performing a parameterization on the plurality of data curves, and determining a regression model for the plurality of data curves.

40. The system according to claim 39, wherein the selection of treatment plans comprises at least one data set of the group consisting of:
   a plurality of structure sets comprising spatial information of a plurality of organs and a target of a corresponding treatment plan of the selection of treatment plans;
   a plurality of pre-optimized treatment plans; and
   a corresponding 3D dose distribution from a plurality of patients of the plurality of previously-optimized treatment plans.

41. The system according to claim 40, wherein performing the parameterization on the plurality of on the plurality of data curves comprises generating a parameter set corresponding to a structure of the plurality of structure sets, a parameter set being comprised from at least one from the group consisting of:
    a plurality of principal components of the DTH;
    a relative overlap volume;
    a relative out-of-field volume;
    an absolute organ at risk volume; and
    an absolute target volume.

* * * * *